US011563345B2

(12) United States Patent
Hall et al.

(10) Patent No.: US 11,563,345 B2
(45) Date of Patent: Jan. 24, 2023

(54) SYSTEMS AND METHODS FOR WIRELESSLY POWERING OR COMMUNICATING WITH STERILE-PACKED DEVICES

(71) Applicant: DePuy Synthes Products, Inc., Raynham, MA (US)

(72) Inventors: Mark Hall, Bridgewater, MA (US); Michael O'Neil, West Barnstable, MA (US); Saurav Gupta, Medway, MA (US)

(73) Assignee: DEPUY SYNTHES PRODUCTS, INC, Raynham, MA (US)

( * ) Notice: Subject to any disclaimer, the term of this patent is extended or adjusted under 35 U.S.C. 154(b) by 0 days.

(21) Appl. No.: 17/545,839

(22) Filed: Dec. 8, 2021

(65) Prior Publication Data

US 2022/0103024 A1    Mar. 31, 2022

Related U.S. Application Data

(63) Continuation of application No. 16/894,245, filed on Jun. 5, 2020, now Pat. No. 11,223,245, which is a
(Continued)

(51) Int. Cl.
*H02J 50/90* (2016.01)
*A61B 5/00* (2006.01)
(Continued)

(52) U.S. Cl.
CPC ............ *H02J 50/90* (2016.02); *A61B 5/0022* (2013.01); *A61B 5/0026* (2013.01); *G16H 40/67* (2018.01);
(Continued)

(58) Field of Classification Search
CPC .......... H04W 76/023; A61F 2007/0077; A61B 5/0026; H02J 50/00; H02J 50/05;
(Continued)

(56) References Cited

U.S. PATENT DOCUMENTS 5,156,162 A    10/1992 Gerhardt
5,251,127 A    10/1993 Raab
(Continued)

FOREIGN PATENT DOCUMENTS

CN            1849101 A    10/2006
CN         101426455 A     5/2009
(Continued)

OTHER PUBLICATIONS

U.S. Appl. No. 14/471,120, filed Aug. 28, 2014, Systems and Methods for Intraoperatively Measuring Anatomical Orientation.
(Continued)

*Primary Examiner* — Curtis B Odom
(74) *Attorney, Agent, or Firm* — Barnes & Thornburg LLP

(57) ABSTRACT

Systems and methods are disclosed herein that can allow for wirelessly powering and/or communicating with a sterile-packed electronic device without removing the electronic device from its sterile packaging and while maintaining the sterility of the electronic device. In some embodiments, a base station with a power transmitter wirelessly transfers power to a power receiver of the electronic device, for example using inductive, capacitive, or ultrasonic coupling. The base station or another external device can also be used to wirelessly program or interrogate the electronic device. Battery charging circuits and switching circuits for use with said systems and methods are also disclosed.

16 Claims, 4 Drawing Sheets

Related U.S. Application Data continuation of application No. 16/515,005, filed on Jul. 17, 2019, now Pat. No. 10,714,987, which is a continuation of application No. 15/375,307, filed on Dec. 12, 2016, now Pat. No. 10,396,606, which is a continuation of application No. 14/983,828, filed on Dec. 30, 2015, now Pat. No. 9,554,411.

(51) Int. Cl.

| | | |
|---|---|---|
| *H02J 50/10* | (2016.01) | |
| *H02J 50/15* | (2016.01) | |
| *H02J 50/30* | (2016.01) | |
| *H02J 50/80* | (2016.01) | |
| *H02J 50/05* | (2016.01) | |
| *H02J 50/12* | (2016.01) | |
| *H02J 50/20* | (2016.01) | |
| *G16H 40/67* | (2018.01) | |
| *H02J 7/00* | (2006.01) | |
| *H04B 5/00* | (2006.01) | |

(52) U.S. Cl.
CPC .......... *H02J 7/00034* (2020.01); *H02J 50/05* (2016.02); *H02J 50/10* (2016.02); *H02J 50/12* (2016.02); *H02J 50/15* (2016.02); *H02J 50/20* (2016.02); *H02J 50/30* (2016.02); *H02J 50/80* (2016.02); *H04B 5/0037* (2013.01); *A61B 2560/0214* (2013.01); *A61B 2562/242* (2013.01)

(58) Field of Classification Search
CPC .. H02J 50/10; H02J 50/12; H02J 50/15; H02J 50/80; H02J 50/90
See application file for complete search history.

(56) References Cited

U.S. PATENT DOCUMENTS

| | | |
|---|---|---|
| 5,291,901 A | 3/1994 | Graf |
| 5,305,203 A | 4/1994 | Raab |
| 5,329,933 A | 7/1994 | Graf |
| 5,748,767 A | 5/1998 | Raab |
| 5,772,610 A | 6/1998 | McGorry et al. |
| 6,015,409 A | 1/2000 | Jackson |
| 6,514,219 B1 | 2/2003 | Guimond et al. |
| 6,565,519 B2 | 5/2003 | Benesh |
| 6,711,432 B1 | 3/2004 | Krause et al. |
| 6,715,213 B2 | 4/2004 | Richter |
| 7,001,346 B2 | 2/2006 | White |
| 7,131,952 B1 | 11/2006 | Dickholtz, Sr. et al. |
| 7,139,601 B2 | 11/2006 | Bucholz et al. |
| 7,335,167 B1 | 2/2008 | Mummy |
| 7,559,931 B2 | 7/2009 | Stone |
| 7,611,522 B2 | 11/2009 | Gorek |
| 7,634,119 B2 | 12/2009 | Tsougarakis et al. |
| 7,634,306 B2 | 12/2009 | Sarin et al. |
| 7,706,000 B2 | 4/2010 | Cohen et al. |
| 7,918,887 B2 | 4/2011 | Roche |
| 7,956,887 B2 | 6/2011 | Hoeg et al. |
| 7,957,809 B2 | 6/2011 | Bourget et al. |
| 7,974,677 B2 | 7/2011 | Mire et al. |
| 7,981,115 B2 | 7/2011 | Justis et al. |
| 8,057,479 B2 | 11/2011 | Stone |
| 8,057,482 B2 | 11/2011 | Stone et al. |
| 8,128,662 B2 | 3/2012 | Altarac et al. |
| 8,167,823 B2 | 5/2012 | Nycz et al. |
| 8,348,954 B2 | 1/2013 | Carls et al. |
| 8,442,621 B2 | 5/2013 | Gorek et al. |
| 8,535,337 B2 | 9/2013 | Chang et al. |
| 8,549,888 B2 | 10/2013 | Isaacs |
| 8,565,853 B2 | 10/2013 | Frigg et al. |
| 8,690,888 B2 | 4/2014 | Stein et al. |
| 8,888,821 B2 | 11/2014 | Rezach et al. |
| 9,198,698 B1 | 12/2015 | Doose et al. |
| 9,554,411 B1 | 1/2017 | Hall et al. |
| 9,579,043 B2 | 2/2017 | Chien et al. |
| 9,993,177 B2 | 6/2018 | Chien et al. |
| 10,335,241 B2 | 7/2019 | Frasier et al. |
| 10,396,606 B2 | 8/2019 | Hall et al. |
| 10,499,996 B2 | 12/2019 | de Almeida Barreto |
| 10,714,987 B2 | 7/2020 | Hall et al. |
| 10,820,835 B2 | 11/2020 | Gupta et al. |
| 11,089,975 B2 | 8/2021 | Frasier et al. |
| 11,160,619 B2 | 11/2021 | Frasier et al. |
| 11,223,245 B2 | 1/2022 | Hall et al. |
| 2002/0035321 A1 | 3/2002 | Bucholz et al. |
| 2002/0120880 A1 | 8/2002 | Simon et al. |
| 2004/0152970 A1 | 8/2004 | Hunter et al. |
| 2005/0033430 A1 | 2/2005 | Powers et al. |
| 2005/0166410 A1 | 8/2005 | Richter et al. |
| 2005/0222793 A1 | 10/2005 | Lloyd et al. |
| 2005/0251026 A1 | 11/2005 | Stone |
| 2005/0262911 A1 | 12/2005 | Dankowicz et al. |
| 2006/0030771 A1 | 2/2006 | Levine et al. |
| 2006/0100508 A1 | 5/2006 | Morrison |
| 2006/0247773 A1 | 11/2006 | Stamp |
| 2007/0060799 A1 | 3/2007 | Lyon et al. |
| 2007/0106146 A1 | 5/2007 | Altmann et al. |
| 2008/0103557 A1 | 5/2008 | Davis et al. |
| 2008/0177203 A1 | 7/2008 | von Jako |
| 2008/0228195 A1 | 9/2008 | von Jako et al. |
| 2008/0266017 A1 | 10/2008 | Simon et al. |
| 2008/0269767 A1 | 10/2008 | O'Brien |
| 2008/0292161 A1 | 11/2008 | Funk et al. |
| 2009/0021752 A1 | 1/2009 | Cohen et al. |
| 2009/0171328 A1 | 7/2009 | Horvath |
| 2009/0249851 A1 | 10/2009 | Isaacs |
| 2010/0010494 A1 | 1/2010 | Quirno |
| 2010/0036384 A1 | 2/2010 | Gorek et al. |
| 2010/0063508 A1 | 3/2010 | Borja et al. |
| 2010/0069919 A1 | 3/2010 | Carls et al. |
| 2010/0087823 A1 | 4/2010 | Kondrashov |
| 2010/0100011 A1 | 4/2010 | Roche |
| 2010/0164296 A1 | 7/2010 | Kurs et al. |
| 2010/0191071 A1 | 7/2010 | Anderson et al. |
| 2010/0191088 A1 | 7/2010 | Anderson et al. |
| 2010/0204575 A1 | 8/2010 | Roche et al. |
| 2010/0204955 A1 | 8/2010 | Roche et al. |
| 2010/0312103 A1 | 12/2010 | Gorek et al. |
| 2011/0040340 A1 | 2/2011 | Miller et al. |
| 2011/0125196 A1 | 5/2011 | Quevedo et al. |
| 2011/0196455 A1 | 8/2011 | Sieracki et al. |
| 2011/0260681 A1 | 10/2011 | Guccione et al. |
| 2011/0270262 A1 | 11/2011 | Justis et al. |
| 2011/0275957 A1 | 11/2011 | Bhandari |
| 2011/0295159 A1 | 12/2011 | Shachar et al. |
| 2012/0035868 A1 | 2/2012 | Roche et al. |
| 2012/0065497 A1 | 3/2012 | Brown et al. |
| 2012/0095330 A1 | 4/2012 | Shechter et al. |
| 2012/0112690 A1 | 5/2012 | Stulen et al. |
| 2012/0123252 A1 | 5/2012 | Brunner |
| 2012/0157019 A1 | 6/2012 | Li |
| 2012/0172653 A1 | 7/2012 | Chornenky et al. |
| 2012/0203140 A1 | 8/2012 | Malchau et al. |
| 2012/0209117 A1 | 8/2012 | Mozes et al. |
| 2012/0232834 A1 | 9/2012 | Roche et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079793 A1 | 3/2013 | Stein et al. |
| 2013/0087950 A1 | 4/2013 | Gunther et al. |
| 2013/0131556 A1 | 5/2013 | Chantz |
| 2013/0135312 A1 | 5/2013 | Yang et al. |
| 2013/0165940 A1 | 6/2013 | DiSilvestro |
| 2013/0241468 A1 | 9/2013 | Moshfeghi |
| 2013/0268007 A1 | 10/2013 | Rezach et al. |
| 2013/0303225 A1 | 11/2013 | Maguire |
| 2013/0345718 A1 | 12/2013 | Crawford et al. |
| 2014/0031829 A1 | 1/2014 | Paradis et al. |
| 2014/0052149 A1 | 2/2014 | van Der Walt et al. |
| 2014/0057572 A1 | 2/2014 | Klinghult et al. |
| 2014/0088607 A1 | 3/2014 | Recknor |
| 2014/0148808 A1 | 5/2014 | Inkpen et al. |

(56) References Cited

U.S. PATENT DOCUMENTS

| | | |
|---|---|---|
| 2014/0171965 A1 | 6/2014 | Loh et al. |
| 2014/0232333 A1 | 8/2014 | Kim et al. |
| 2014/0273833 A1 | 9/2014 | McCormack et al. |
| 2014/0275940 A1 | 9/2014 | Hladio et al. |
| 2014/0275981 A1 | 9/2014 | Selover et al. |
| 2014/0276871 A1 | 9/2014 | Sherman et al. |
| 2014/0303522 A1 | 10/2014 | Akimoto et al. |
| 2014/0330112 A1 | 11/2014 | Wasielewski |
| 2015/0011874 A1 | 1/2015 | Amoako-Tuffour et al. |
| 2015/0057733 A1 | 2/2015 | Lotfi |
| 2015/0137746 A1 | 5/2015 | Lee et al. |
| 2015/0142372 A1 | 5/2015 | Singh |
| 2015/0150646 A1 | 6/2015 | Pryor et al. |
| 2015/0180263 A1 | 6/2015 | Sud et al. |
| 2015/0185846 A1 | 7/2015 | Otto et al. |
| 2015/0272694 A1 | 10/2015 | Charles |
| 2015/0305786 A1 | 10/2015 | Wehrle et al. |
| 2015/0313482 A1 | 11/2015 | Nabutovsky et al. |
| 2015/0313566 A1 | 11/2015 | Diers et al. |
| 2016/0007909 A1 | 1/2016 | Singh et al. |
| 2016/0058320 A1 | 3/2016 | Chien et al. |
| 2016/0058523 A1 | 3/2016 | Chien et al. |
| 2016/0191887 A1 | 6/2016 | Casas |
| 2016/0225192 A1 | 8/2016 | Jones et al. |
| 2016/0235480 A1 | 8/2016 | Scholl et al. |
| 2016/0262800 A1 | 9/2016 | Scholl et al. |
| 2016/0360997 A1 | 12/2016 | Yadav et al. |
| 2017/0143426 A1 | 5/2017 | Isaacs et al. |
| 2017/0189121 A1 | 7/2017 | Frasier et al. |
| 2017/0194820 A1 | 7/2017 | Hall et al. |
| 2017/0196507 A1 | 7/2017 | Singh et al. |
| 2017/0231709 A1 | 8/2017 | Gupta et al. |
| 2017/0348061 A1 | 12/2017 | Joshi et al. |
| 2018/0070860 A1 | 3/2018 | Gupta et al. |
| 2018/0256067 A1 | 9/2018 | Chien et al. |
| 2018/0279913 A1 | 10/2018 | Frasier et al. |
| 2019/0090955 A1 | 3/2019 | Singh et al. |
| 2019/0321109 A1 | 10/2019 | Frasier et al. |
| 2019/0341818 A1 | 11/2019 | Hall et al. |
| 2020/0297432 A1 | 9/2020 | Frasier et al. |
| 2020/0303971 A1 | 9/2020 | Hall et al. |
| 2021/0059563 A1 | 3/2021 | Gupta et al. |
| 2021/0338107 A1 | 11/2021 | Frasier et al. |
| 2022/0103024 A1 | 3/2022 | Hall et al. |

FOREIGN PATENT DOCUMENTS

| | | |
|---|---|---|
| CN | 102694421 A | 9/2012 |
| CN | 103385708 A | 11/2013 |
| CN | 103748763 A | 4/2014 |
| CN | 104854533 A | 8/2015 |
| CN | 105011977 A | 11/2015 |
| CN | 105378820 B | 2/2018 |
| EP | 1943954 A2 | 7/2008 |
| EP | 2597783 A2 | 5/2013 |
| EP | 2901957 A1 | 8/2015 |
| GB | 190927693 A | 9/1910 |
| JP | 2000254141 A | 9/2000 |
| JP | 2003523795 A | 8/2003 |
| JP | 2005095433 A | 4/2005 |
| JP | 3746628 B2 | 2/2006 |
| JP | 4323276 B2 | 9/2009 |
| JP | 2009273521 A | 11/2009 |
| JP | 2010233354 A | 10/2010 |
| JP | 2012120648 A | 6/2012 |
| JP | 2013544144 A | 12/2013 |
| JP | 2015502766 A | 1/2015 |
| JP | 2015109785 A | 6/2015 |
| JP | 2015213753 A | 12/2015 |
| JP | 2017510307 A | 4/2017 |
| WO | 1991003980 A1 | 4/1991 |
| WO | 1999015097 A2 | 4/1999 |
| WO | 2005077000 A2 | 8/2005 |
| WO | 2013053398 A1 | 4/2013 |
| WO | 2013169674 A1 | 11/2013 |
| WO | 2014025305 A1 | 2/2014 |
| WO | 2014063181 A1 | 5/2014 |
| WO | 2015003224 A1 | 1/2015 |
| WO | 2015114119 A1 | 8/2015 |
| WO | 2015162965 A1 | 10/2015 |
| WO | 2016032875 A1 | 3/2016 |
| WO | 2019055912 A1 | 3/2019 |

OTHER PUBLICATIONS

U.S. Appl. No. 14/934,237, filed Nov. 6, 2015, Systems and Methods for Intraoperatively Measuring Anatomical Orientation.

U.S. Appl. No. 14/983,818, filed Dec. 30, 2015, Method and Apparatus for Intraoperative Measurements of Anatomical Orientation.

U.S. Appl. No. 14/983,828, filed Dec. 30, 2015, Systems and Methods for Wirelessly Powering or Communicating With Sterile-Packed Devices.

U.S. Appl. No. 15/263,023, filed Sep. 12, 2016, Systems and Methods for Anatomical Alignment.

U.S. Appl. No. 15/375,307, filed Dec. 12, 2016, Systems and Methods for Wirelessly Powering or Communicating With Sterile-Packed Devices.

U.S. Appl. No. 15/429,566, filed Feb. 10, 2017, Systems and Methods for Intraoperatively Measuring Anatomical Orientation.

U.S. Appl. No. 15/475,587, filed Mar. 31, 2017, Systems, Devices and Methods for Enhancing Operative Accuracy Using Inertial Measurement Units.

U.S. Appl. No. 15/976,482, filed May 10, 2018, Stems and Methods for Intraoperatively Measuring Anatomical Orientation.

U.S. Appl. No. 16/434,166, filed Jun. 6, 2019, Method and Apparatus for Intraoperative Measurements of Anatomical Orientation.

U.S. Appl. No. 16/515,005, filed Jul. 17, 2019, Systems and Methods for Wirelessly Powering or Communicating With Sterile-Packed Devices.

U.S. Appl. No. 16/892,955, filed Jun. 4, 2020, Method and Apparatus for Intraoperative Measurements of Anatomical Orientation.

U.S. Appl. No. 16/894,245, filed Jun. 5 2020, Systems and Methods for Wirelessly Powering or Communicating With Sterile-Packed Devices.

U.S. Appl. No. 17/066,472, filed Oct. 8, 2020, Systems and Methods for Anatomical Alignment.

U.S. Appl. No. 17/378,639, dated Jul. 16, 2021, Systems, Devices and Methods for Enhancing Operative Accuracy Using Inertial Measurement Units.

U.S. Appl. No. 17/509,665, filed Oct. 25, 2021, Method and Apparatus for Intraoperative Measurements of Anatomical Orientation.

Baka, Nora, et al. "2D-3D shape reconstruction of the distal femur from stereo X-ray imaging using statistical shape models," Medical image analysis 15.6 (2011): 840-850.

Conn, K. S., M. T. Clarke, and J.P. Hallett, "A Simple Guide to Determine the Magnification of Radiographs and to Improve the Accuracy of Preoperative Templating," Bone & Joint Journal 84.2 (2002): 269-272.

Delorme, et al., Intraoperative comparison of two instrumentation techniques for the correction of adolescent diopathic scoliosis. Rod rotation and translation Spine (Phila Pa 1976). Oct. 1, 1999;24(19):2011-7.

Extended European Search Report for Application No. 17849374.8, dated Mar. 31, 2020 (8 pages).

Ghanem, et al., Intraoperative optoelectronic analysis of three-dimensional vertebral displacement after Cotrel-Dubousset rod rotation. A preliminary report. Spine (Phila Pa 1976) Aug. 15, 1997;22(16):1913-21.

Gorski, J.M., and Schwartz, L. "A Device to Measure X-ray Magnification in Preoperative Planning for Cementless Arthroplasty," Clinical Orthopaedics and Related Research 202 (1986): 302-306.

Australian Office Action for Application No. 2016380934, dated Sep. 16, 2020 (6 pages).

Australian Office Action for Application No. 2016380934, dated Feb. 5, 2021, (5 pages).

(56) References Cited

OTHER PUBLICATIONS

Chinese Office Action for Application No. 201680077321.9, dated Jan. 6, 2021 (17 pages).
Chinese Supplemental Search Report for Application No. 201680077321.9, dated Dec. 5, 2021 (1 page).
Chinese Office Action for Application No. 201780055976.0, dated Mar. 24, 2021 (22 pages).
Chinese Supplemental Search Report for Application No. 201780055976.0, dated Nov. 20, 2021 (1 page).
International Search Report and Written Opinion for Application No. PCT/US2015/046217, dated Nov. 9, 2015 (11 pages).
International Search Report and Written Opinion for Application No. PCT/US2016/067134, dated Sep. 11, 2017 (20 pages).
International Search Report and Written Opinion for Application No. PCT/US2016/067140, dated Mar. 23, 2017 (13 pages).
International Search Report and Written Opinion for Application No. PCT/US2017/017344, dated Jul. 13, 2017 (22 pages).
International Search Report for Application No. PCT/US2017/050023, dated Jan. 8, 2018 (6 Pages).
International Search Report and Written Opinion for Application No. PCT/US2018/024791, dated Aug. 6, 2018 (12 pages).
Invitation to Pay Additional Fees for Application No. PCT/US2016/067134, dated Jun. 26, 2017 (14 pages).
Japanese Office Action for Application No. 2018-534634, dated Nov. 10, 2020 (12 pages).
Japanese Office Action for Application No. 2019-513849, dated Jun. 8, 2021 (6 pages).
Japanese Office Action for Application No. 2019-553503, dated Dec. 14, 2021 (10 pages).
King, R. J., et al. "A Novel Method of Accurately Calculating the Radiological Magnification of the Hip," Bone & Joint Journal 91.9 (2009): 1217-1222.
Lafon, et al., Intraoperative three dimensional correction during in situ contouring surgery by using a numerical model. Spine (Phila Pa 1976). Feb. 15, 2010;35(4):453-9. doi: 10.1097/BRS.0b013e3181b8eaca. Abstract.
Lafon, et al., Intraoperative three-dimensional correction during rod rotation technique. Spine (Phila Pa 1976). Mar. 1, 2009;34(5):512-9. doi: 10.1097/BRS.0b013e31819413ec.
Lamecker, Hans, Thomas H. Wenckebach, and H-C. Hege. "Atlas-based 3D-shape reconstruction from X-ray images," Pattern Recognition, 2006. ICPR 2006. 18th International Conference on. vol. 1. IEEE, 2006; pp. 1-4.
Luc Duong, et al., Real time noninvasive assessment of external trunk geometry during surgical correction of adolescent idiopathic scoliosis. Scoliosis. Feb. 24, 2009;4:5. doi: 10.1186/1748-7161-4-5.
Mac-Thiong, et al., A new technique for intraoperative analysis of trunk geometry in adolescent idiopathic scoliosis. Can J Surg. Jun. 2002;45(3):219-23.
Mac-Thiong, et al., The effect of intraoperative traction during posterior spinal instrumentation and fusion for adolescent idiopathic scoliosis. Spine (Phila Pa 1976). Jul. 15, 2004;29(14):1549-54.
Markelj, Primoz, et al. "A review of 3D/2D registration methods for image-guided interventions," Medical image analysis 16.3 (2012): 642-661.
Mazzilli, F., et al. "Ultrasound Energy Harvesting System for Deep Implanted-Medical-Devices (IMDs)", 2012 IEEE International Symposium on Circuits and Systems (ISCAS),Seoul, 2012, pp. 2865-2868.
Sarkalkan, Nazli, Harrie Weinans, and Amir A. Zadpoor, "Statistical shape and appearance models of bones," Bone 60 (2014): 129-140.
Schumann, S., Thelen, B., Ballestra, S., Nolte, L. P., Buehler, P., & Zheng, G., "X-ray Image Calibration and Its Application to Clinical Orthopedics," Medical Engineering & Physics (2014): 36(7), 968-974.
The, B., et al., "Digital Correction of Magnification in Pelvic X-rays for Preoperative Planning of Hip Joint Replacements: Theoretical Development and Clinical Results of a New Protocol," Medical Physics 32.8 (2005): 2580-2589.
Written Opinion for Application No. PCT/US2017/050023, dated Jan. 8, 2018 (J&J No. MED5026WOPCT) (4 Pages).
Zheng, Guoyan, et al., "A 2D/3D correspondence building method for reconstruction of a patient-specific 3D bone surface model using point distribution models and calibrated X-ray images," Medical image analysis 13.6 (2009): 883-899.

SYSTEMS AND METHODS FOR WIRELESSLY POWERING OR COMMUNICATING WITH STERILE-PACKED DEVICES

CROSS-REFERENCE TO RELATED APPLICATIONS

This application is a continuation of and claims priority to U.S. application Ser. No. 16/894,245, filed on Jun. 5, 2020. U.S. application Ser. No. 16/894,245 is a continuation of and claims priority to U.S. application Ser. No. 16/515,005, filed on Jul. 17, 2019, and now issued as U.S. Pat. No. 10,714, 987. U.S. application Ser. No. 16/515,005 is a continuation of and claims priority to U.S. application Ser. No. 15/375, 307, filed on Dec. 12, 2016, and now issued as U.S. Pat. No. 10,396,606. U.S. application Ser. No. 15/375,307 is a continuation of and claims priority to U.S. application Ser. No. 14/983,828, filed on Dec. 30, 2015, and now issued as U.S. Pat. No. 9,554,411. Each of these applications is hereby incorporated by reference in its entirety.

FIELD

Systems and methods for wirelessly powering or communicating with sterile-packed devices are disclosed herein.

BACKGROUND

It is increasingly common for electronic devices to be used in surgical or other medical procedures. Electronic devices can provide a variety of useful benefits in this setting, but can also introduce certain challenges.

For example, electronic devices that are powered by an internal battery generally require that the battery be charged prior to use. The battery can be partially or completely drained, however, while the device is sitting on the shelf waiting to be used in a procedure. Charging the battery during the medical procedure can undesirably introduce delays and disrupt the flow of the procedure. It is also difficult to charge the battery of the electronic device while maintaining sterility of the electronic device. Attempts to minimize this problem by equipping the electronic device with a higher capacity battery result in the electronic device being larger and/or heavier. Larger devices are generally undesirable, as the available space to maneuver the device during the procedure can be limited. Similarly, heavier devices are generally undesirable, as the added weight can contribute to surgeon fatigue or reduce the ability to finely control movement and positioning of the device.

By way of further example, some electronic devices require programming with patient-specific or procedure-specific data or instructions. The step of programming the device before use can lengthen the medical procedure or disrupt the flow of the procedure. The programming step can further drain the battery, exacerbating the issues described above. Also, in the case of sterile electronic devices, it is difficult to program the device while maintaining its sterility.

As another example, once an electronic device is sterilized and/or packed in a sterile container, it generally cannot be tested, calibrated, identified, etc. without opening the sterile packaging.

SUMMARY

Systems and methods are disclosed herein that can allow for wirelessly powering and/or communicating with a sterile-packed electronic device without removing the electronic device from its sterile packaging and while maintaining the sterility of the electronic device. In some embodiments, a base station with a power transmitter wirelessly transfers power to a power receiver of the electronic device, for example using inductive, capacitive, or ultrasonic coupling. The base station or another external device can also be used to wirelessly program or interrogate the electronic device. Battery charging circuits and switching circuits for use with said systems and methods are also disclosed.

In some embodiments, a surgical method includes aligning a power receiver of a surgical electronic device with a power transmitter of a base station; wirelessly transferring power from the power transmitter to the power receiver through a sterile container in which the electronic device is disposed; upon receipt of wireless power, automatically initiating communications with the base station; and wirelessly communicating medical data to the electronic device from the base station.

The surgical electronic device can include at least one of an instrument and an implant.

Aligning the power receiver can include aligning a graphical mark formed on the base station with a corresponding graphical mark formed on the sterile container.

Aligning the power receiver with the power transmitter can include positioning the sterile container in a recess defined in the base station.

The sterile container can be configured to maintain the power receiver in a fixed position with respect to the sterile container.

The sterile container can include an inner blister pack in which the electronic device is disposed, an outer blister pack in which the inner blister pack is disposed, and an outer box in which the outer blister pack is disposed.

The method can include switching to battery power when the device is ready for use.

Said switching can occur automatically when the electronic device is removed from the sterile container.

The medical data can include at least one of patient-specific data, an operative plan, surgical correction information, and device calibration information.

The method can include communicating device data from the electronic device to the base station.

The device data can include at least one of device identification information, device diagnostic information, and device charge level information.

Transferring the power can be effective to charge a battery of the electronic device.

Transferring the power can include driving an ultrasonic transducer of the base station to generate ultrasonic waves received at an ultrasonic transducer of the electronic device.

Transferring the power can include generating a magnetic field between a primary coil of the power transmitter and a secondary coil of the power receiver.

Transferring the power can include generating an electric field between an electrode of the power transmitter and an electrode of the power receiver.

The power transmitter can include a light source and transferring the power can include directing light from the light source through the sterile container to a photovoltaic cell of the electronic device.

The method can include, after said transferring and communicating steps, opening the sterile container and using the electronic device in a surgical procedure.

The electronic device can include a sensor configured to sense a position or orientation of the electronic device.

The method can include rectifying an AC signal received at the power receiver with a full wave rectifier and applying the signal to a capacitor of the electronic device wired in parallel with a battery of the electronic device to charge the battery.

The method can include wirelessly communicating measurements or other data captured during a surgical procedure from the electronic device to the base station after the surgical procedure is performed.

In some embodiments, a system includes an electronic device having a wireless power receiver and a sensor configured to detect a position or orientation of the electronic device; a sterile container in which the electronic device is disposed such that the sterile device is completely surrounded by the sterile container; and a base station having a wireless power transmitter, the wireless power transmitter being configured to transfer power through the sterile container to the wireless power receiver of the electronic device.

The electronic device can include at least one of an instrument and an implant.

The sterile container can include a graphical mark positioned with respect to the power receiver such that, when the graphical mark of the sterile container is aligned with a graphical mark of the base station, the power receiver is aligned with the power transmitter.

The base station can include a recess positioned with respect to the power transmitter such that, when the sterile container is seated in the recess, the power transmitter is aligned with the power receiver.

The sterile container can be configured to maintain the power receiver in a fixed position with respect to the sterile container.

The sterile container can include an inner blister pack in which the electronic device is disposed, an outer blister pack in which the inner blister pack is disposed, and an outer box in which the outer blister pack is disposed.

The electronic device can include a switch configured to switch between a first operating mode in which the electronic device is powered by the power receiver and a second operating mode in which the electronic device is powered by an internal battery.

The switch can be configured to switch from the first operating mode to the second operating mode automatically when the electronic device is removed from the sterile container.

The base station can include a communications interface configured to wirelessly transmit medical data to a communications interface of the electronic device, the medical data comprising at least one of patient-specific data, an operative plan, surgical correction information, and device calibration information.

The electronic device can include a communications interface configured to wirelessly transmit device data to a communications interface of the base station, the device data comprising at least one of device identification information, device diagnostic information, and device charge level information.

The power transmitter can include an ultrasonic transducer configured to generate ultrasonic waves received at an ultrasonic transducer of the power receiver to wirelessly transfer power from the base station to the electronic device.

The power transmitter can include a primary coil configured to generate a magnetic field between the primary coil and a secondary coil of the power receiver to wirelessly transfer power from the base station to the electronic device.

The power transmitter can include an electrode configured to generate an electric field between the electrode and an electrode of the power receiver to wirelessly transfer power from the base station to the electronic device.

The power receiver can include a full wave rectifier that rectifies an AC signal received at the power receiver and applies the signal to a capacitor of the electronic device wired in parallel with a battery of the electronic device to charge the battery.

The present invention further provides systems and methods as claimed.

BRIEF DESCRIPTION OF THE DRAWINGS

The invention will be more fully understood from the following detailed description taken in conjunction with the accompanying drawings, in which.

DETAILED DESCRIPTION

Systems and methods are disclosed herein that can allow for wirelessly powering and/or communicating with a sterile-packed electronic device without removing the electronic device from its sterile packaging and while maintaining the sterility of the electronic device. In some embodiments, a base station with a power transmitter wirelessly transfers power to a power receiver of the electronic device, for example using inductive, capacitive, or ultrasonic coupling. The base station or another external device can also be used to wirelessly program or interrogate the electronic device. Battery charging circuits and switching circuits for use with said systems and methods are also disclosed.

Certain exemplary embodiments will now be described to provide an overall understanding of the principles of the structure, function, manufacture, and use of the systems and methods disclosed herein. One or more examples of these embodiments are illustrated in the accompanying drawings. Those of skill in the art will understand that the systems and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1:
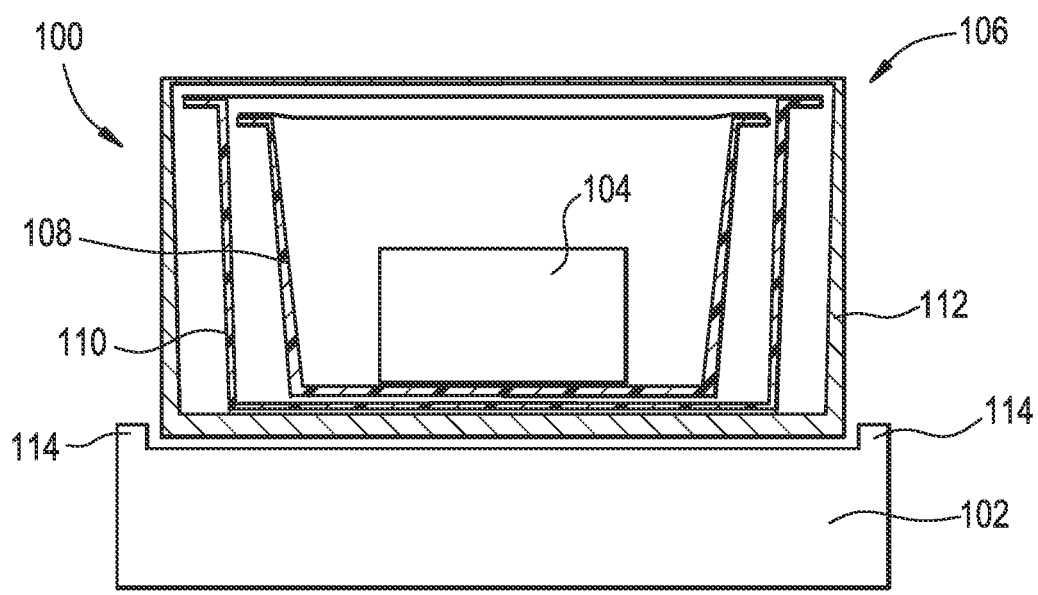
FIG. 1 is a sectional side view of a system for wirelessly powering or communicating with an electronic device.

FIG. 1 illustrates an exemplary system 100 for wirelessly powering or communicating with an electronic device. The system 100 generally includes a base station 102 with a power transmitter configured to wirelessly transmit power to an electronic device 104 with a corresponding power receiver. As detailed below, various systems can be employed for wirelessly powering the electronic device, including inductive, capacitive, and ultrasonic systems. The base station can also include a communications unit for wirelessly communicating with a corresponding communications unit of the electronic device. Accordingly, the base station can transmit programming information to the electronic device, receive diagnostic or identification information from the electronic device, or communicate in other ways with the electronic device.

The electronic device 104 can be sterilized and/or packed in a sterile container 106. It will be appreciated that any of a variety of containers for maintaining a sterile barrier between the electronic device and the surrounding environment can be used. The container 106 can be fluid-tight, air-tight, and/or liquid-tight. The sterile container 106 can be configured to completely surround or encase the electronic device 104, for example, such that the electronic device is disposed in an enclosed, sealed volume defined by the sterile container. In some embodiments, the sterile container 106 is not formed by living tissue. The sterile container 106 can be separate and distinct from an outermost housing of the electronic device 104.

In the illustrated embodiment, the sterile container 106 includes an inner blister pack 108, an outer blister pack 110, and an outer box 112. The outer box 112 is generally not sterile and is used for general shipping and handling of the electronic device 104 leading up to its use in a medical procedure. Exemplary outer boxes are formed from cardboard or paper. The blister packs 108, 110 each include a tray that is bonded or adhered to a lid to define a closed interior volume. The tray and the lid can be formed from any of a variety of materials, including plastic or foil. The interior of the outer blister pack 110 is sterile, while the exterior of the outer blister pack is generally not sterile. The inner blister pack 108 is sterile on the exterior such that it can be handled in a sterile field. The inner blister pack 108 is also sterile on the interior, as is the electronic device 104 contained therein. In use, the outer box 112 is typically removed and the electronic device 104 is staged for the medical procedure in the inner and outer blister packs 108, 110. The outer blister pack 110 is then opened and the sterile inner blister pack 108 is dropped into the sterile field. Finally, the inner blister pack 108 is opened in the sterile field and the sterile electronic device 104 contained therein is removed for use in the procedure.

Figure 2:
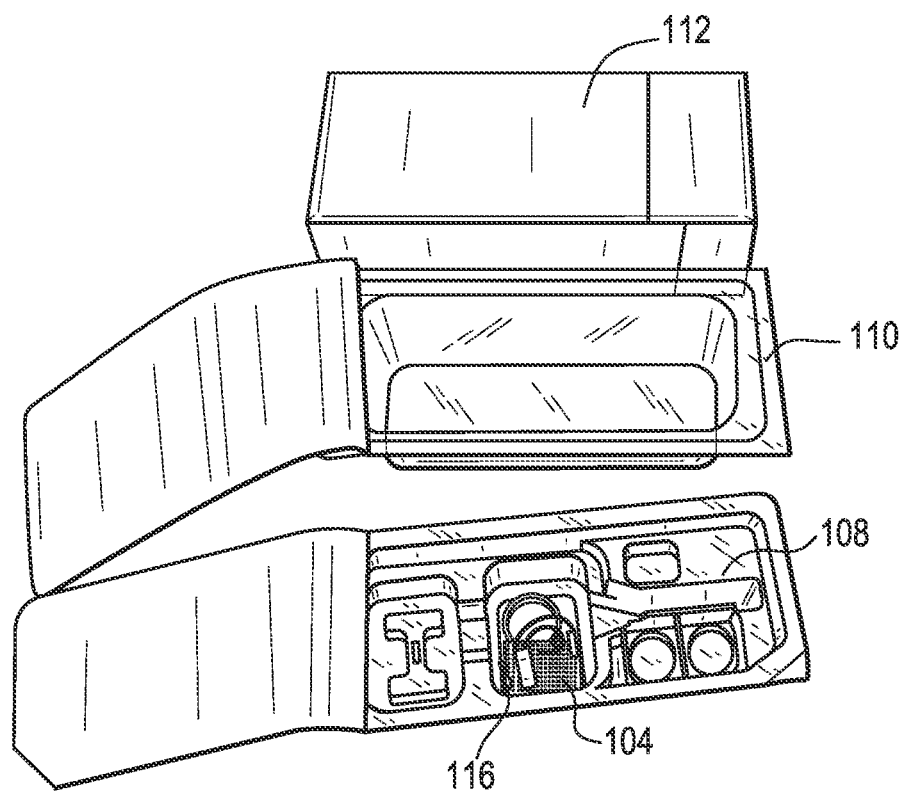
FIG. 2 is a perspective view of a sterile package for an electronic device, shown in an open configuration.
Figure 3:
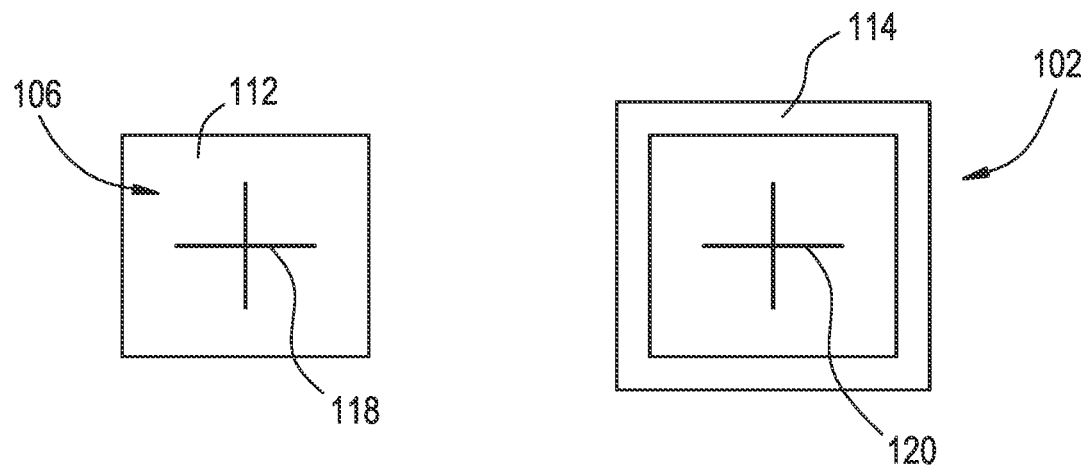
FIG. 3 is a top view of a base station and a sterile package for an electronic device.

In some embodiments (e.g., the inductive and capacitive systems described below), it can be important to maintain precise alignment between the transmitter and receiver to maximize power transfer efficiency. To facilitate alignment, the base station 102 can include a perimeter rim or other surface recesses or projections 114. The geometry of these alignment features can be selected to correspond to that of the sterile package 106 of the electronic device 104 with which the base station 102 is to be used. The sterile package 106 can also have internal baffles or cutouts 116, e.g., as shown in FIG. 2, configured to maintain the electronic device 104 contained therein in a fixed position relative to the sterile packaging. Accordingly, simply placing the sterile package 106 within the contour defined by the base station 102 can ensure that the transmitter and receiver are precisely aligned. Alternatively, or in addition, the electronic device 104 or its sterile packaging 106 can include a graphical marking 118 that can be aligned by the user with a corresponding graphical marking 120 on the base station 102 to ensure that the transmitter and receiver are aligned (e.g., as shown in FIG. 3).

The electronic device can take various forms. Exemplary electronic devices include implants, surgical instruments, diagnostic instruments, durable medical equipment, and the like. The electronic device can be or can include surgical electronic modules of the type described in U.S. patent application Ser. No. 14/471,120 filed on Aug. 28, 2014 and entitled "SYSTEMS AND METHODS FOR INTRAOPERATIVELY MEASURING ANATOMICAL ORIENTATION," now issued as U.S. Pat. No. 9,993,177 on Jun. 12, 2018, which is hereby incorporated by reference in its entirety, said modules being adapted in accordance with the teachings herein.

Figure 4:
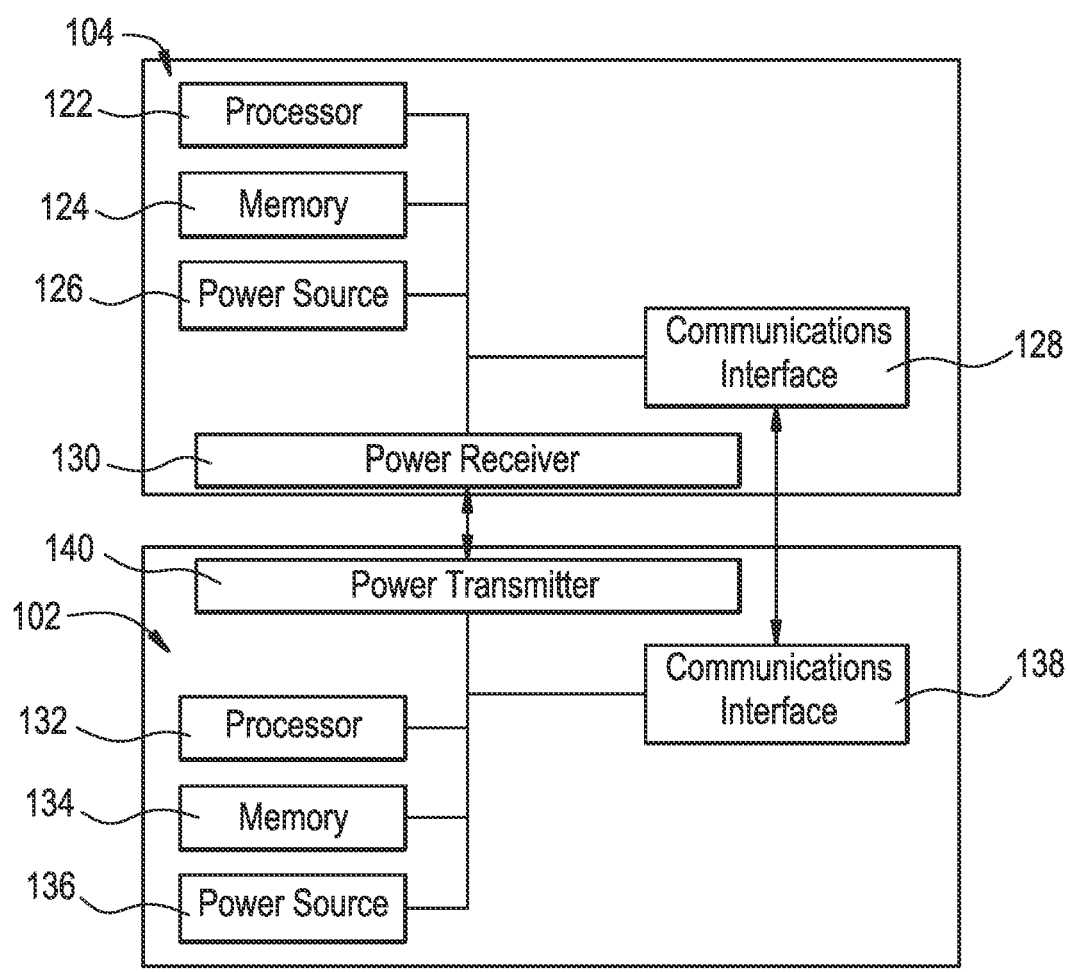
FIG. 4 is a schematic block diagram of an electronic device and a base station.

An exemplary electronic device 104 is schematically illustrated in FIG. 4. As shown, the electronic device 104 can include a processor 122, a memory 124, a power source 126, a communications interface 128, and a power receiver 130, any one or more of which can be in communication with each other. The electronic device 104 can also include other features not shown in FIG. 4, such as a display, buttons or other user interface elements, and/or a sensor (e.g., for sensing a physiological parameter of a patient, for sensing a position and orientation of the electronic device, or for sensing some other parameter of the electronic device). Exemplary sensors can include an accelerometer, a gyroscopic sensor, a geomagnetic sensor, and ultrasound, electromagnetic, and/or infrared transceivers for communicating with a positioning system, as well as temperature sensors, pressure sensors, strain sensors, and biosensors.

The processor 122 can include a microcontroller, a microcomputer, a programmable logic controller (PLC), a field-programmable gate array (FPGA), an application specific integrated circuit (ASIC), integrated circuits generally referred to in the art as a computer, and other programmable circuits, and these terms are used interchangeably herein. The processor 122 can be configured to control operation of the electronic device 104, for example by executing instructions stored in the memory 124 or by performing calculations or evaluations based on data output from a sensor or received via the communications interface 128.

The processor 122 can be coupled to the memory 124, which can include a random access memory (RAM), a read-only memory (ROM), a flash memory, a non-transitory computer readable storage medium, and so forth. The memory 124 can store instructions for execution by the processor 122 to implement the functionality of the electronic device 104. The memory 124 can also store information sensed by a sensor, the result of calculations performed by the processor 122, or information received from an external device through the communications interface 128.

The power source 126 can be configured to provide power to the various electronic components of the device 104. The power source 126 can include an internal battery, which can be a lithium-ion battery or any other battery known in the art, or other power storage devices such as capacitor arrays and the like.

The communications interface 128 can be configured to receive information from an external device or to transmit information to an external device. For example, the communications interface 128 can permit two-way communication with the base station 102, or with other external devices. The communications interface 128 can be wireless (e.g., near-field communication (NFC), Wi-Fi, Bluetooth, Bluetooth LE, ZigBee, and the like) or wired (e.g., USB or Ethernet). In the case of NFC, for example, the electronic device 104 can include a radio transceiver configured to communicate with a radio transceiver of another device, e.g., the base station 102 or a second electronic device, using one or more standards such as ISO/IEC 14443, FeliCa, ISO/IEC 18092, and those defined by the NFC Forum. The communication interface 128 can be selected to provide the desired communication range. In some embodiments, Bluetooth (e.g., class 2 Bluetooth having a range of 5-10 meters) can be used for the communication interface 128 to allow the electronic device 104 to remain somewhat distant from the device with which it is communicating, e.g., the base station 102, while at the same time limiting the communication range such that other electronic devices unlikely to be used in the surgery are not needlessly involved.

The communications interface 128 can be integrated with or coupled to the power receiver 130 such that information can be embedded or encoded in the wireless power signal received and/or sent by the electronic device 104. For example, information can be communicated to or from the electronic device 104 by encoding the information in the wireless power signal using frequency modulation, frequency-domain multiplexing, frequency shift keying, amplitude modulation, phase modulation, analog or digital modulation techniques, and/or combinations thereof. The communications interface 128 can include filters or other circuit elements for extracting information from the power signal or embedding information in the power signal.

The power receiver 130 can be configured to receive wireless power from the base station 102, e.g., as detailed below with respect to FIGS. 5-7.

It will be appreciated that any one or more of the above components can be omitted from the electronic device 104, and the electronic device can include more components than what is shown in FIG. 4. In another exemplary embodiment, the electronic device 104 can include a motor, a power source, and a power receiver.

An exemplary base station 102 is also shown schematically in FIG. 4. As demonstrated by the illustrated embodiment, the base station 102 can include a processor 132, a memory 134, a power source 136, a communications interface 138, and a power transmitter 140, any one or more of which can be in communication with each other. The base station 102 can also include other features not shown in FIG. 4, such as a display, buttons, or other user interface elements.

The processor 132 can include a microcontroller, a microcomputer, a programmable logic controller (PLC), a field-programmable gate array (FPGA), an application specific integrated circuit (ASIC), integrated circuits generally referred to in the art as a computer, and other programmable circuits, and these terms are used interchangeably herein. The processor 132 can be configured to control operation of the base station 102, for example by executing instructions stored in the memory 134 or by performing calculations or evaluations based on data received via the communications interface 138.

The processor 132 can be coupled to the memory 134, which can include a random access memory (RAM), a read-only memory (ROM), a flash memory, a non-transitory computer readable storage medium, and so forth. The memory 134 can store instructions for execution by the processor 132 to implement the functionality of the base station 102. The memory 134 can also store the result of calculations performed by the processor 132, or information received from an electronic device 104 through the communications interface 138.

The power source 136 can be configured to provide power to the various electronic components of the base station 102.

The power source 136 can include an internal battery, which can be a lithium-ion battery or any other battery known in the art, other power storage devices such as capacitor arrays and the like, or an external power source coupled to the base station 102 via an adaptor, e.g., via a USB port, AC adapter/transformer, wall charger, etc.

The communications interface 138 can be configured to receive information from an external device or to transmit information to an external device. For example, the communications interface 138 can permit two-way communication with the electronic device 104, or with other external devices. The communications interface 138 can be wireless (e.g., near-field communication (NFC), Wi-Fi, Bluetooth, Bluetooth LE, ZigBee, and the like) or wired (e.g., USB or Ethernet). In the case of NFC, for example, the base station 102 can include a radio transceiver configured to communicate with a radio transceiver of another device, e.g., the electronic device 104, using one or more standards such as ISO/IEC 14443, FeliCa, ISO/IEC 18092, and those defined by the NFC Forum. The communication interface 138 can be selected to provide the desired communication range. In some embodiments, Bluetooth (e.g., class 2 Bluetooth having a range of 5-10 meters) can be used for the communication interface 138 to allow the base station 102 to remain somewhat distant from the device with which it is communicating, e.g., the electronic device 104, while at the same time limiting the communication range such that other electronic devices unlikely to be used in the surgery are not needlessly involved.

The communications interface 138 can be integrated with or coupled to the power transmitter 140 such that information can be embedded or encoded in the wireless power signal received and/or sent by the base station 102. For example, information can be communicated to or from the base station 102 by encoding the information in the wireless power signal using frequency modulation, frequency-domain multiplexing, frequency shift keying, amplitude modulation, phase modulation, analog or digital modulation techniques, and/or combinations thereof. The communications interface 138 can include filters or other circuit elements for extracting information from the power signal or embedding information in the power signal.

The power transmitter 140 can be configured to transmit wireless power to the electronic device 104, e.g., as detailed below with respect to FIGS. 5-7.

It will be appreciated that any one or more of the above components can be omitted from the base station 102, and the base station can include more components than what is shown in FIG. 4.

Figure 5:
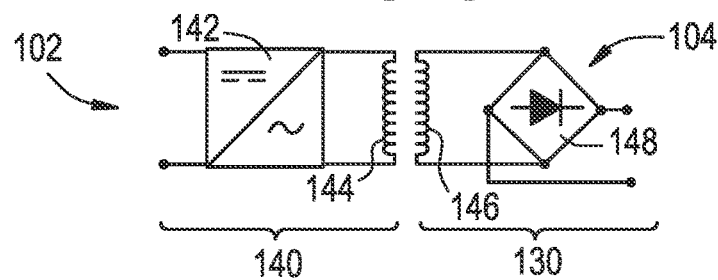
FIG. 5 is a schematic circuit diagram of an inductive wireless power system.
Figure 6:
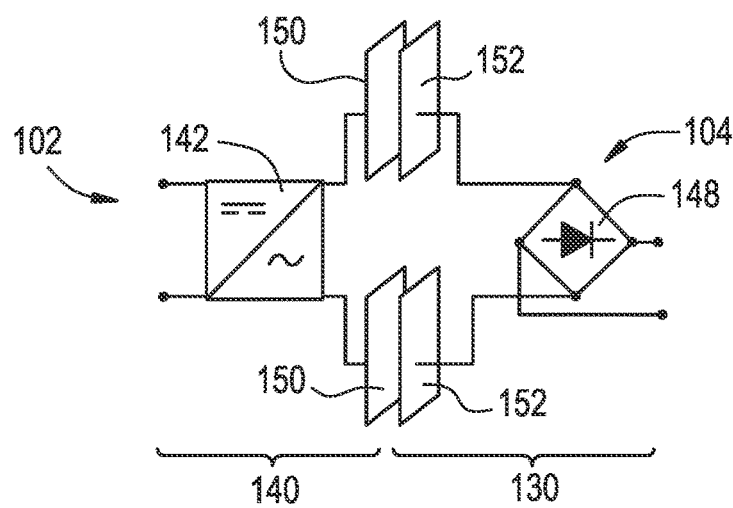
FIG. 6 is a schematic circuit diagram of a capacitive wireless power system.
Figure 7:
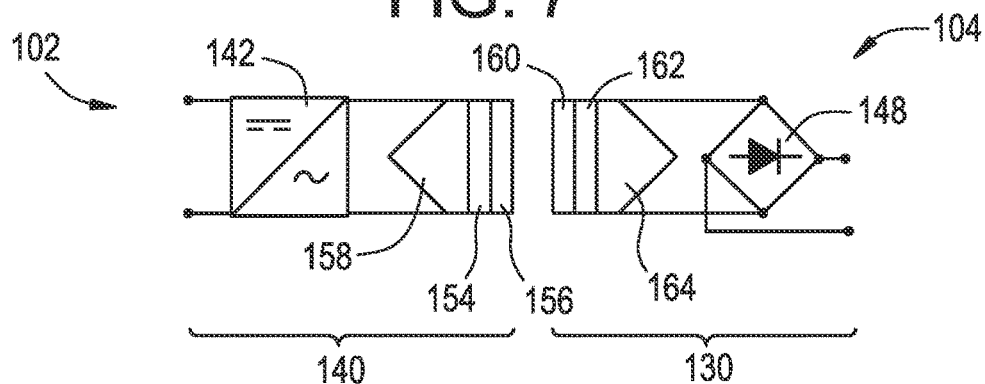
FIG. 7 is a schematic circuit diagram of an ultrasonic wireless power system.

FIGS. 5-7 illustrate exemplary systems that can be used to wirelessly transfer power from the base station 102 to the electronic device 104 or, in some embodiments, from the electronic device to the base station. While inductive, capacitive, and ultrasound wireless power transfer schemes are described below, it will be appreciated that other schemes can be used, such as electromagnetic radiation, resonant inductive coupling, magnetodynamic coupling, microwaves, radio waves, lasers, infrared or visible light waves, and so forth. It will further be appreciated that the system 100 can employ multiple of these schemes, operating in combination with one another or as selectable alternatives.

FIG. 5 illustrates an exemplary power transfer scheme in which the power transmitter 140 of the base station 102 uses inductive coupling to provide power to the power receiver 130 of the electronic device 104.

As shown, the base station 102 generally includes an inverter 142 that converts a DC input provided by the power source 136 into an AC signal which is in turn applied to a primary coil 144 to generate an oscillating magnetic field. The electronic device 104 includes a secondary coil 146 in which an AC signal is induced by the magnetic field generated at the primary coil 144. The AC signal is converted by a rectifier 148 to a DC output that can be used to power the processor 122, memory 124, communications interface 128, or other components of the electronic device 104, or to charge a battery 126 of the electronic device. When the base station 102 is coupled to an AC mains current or other source of AC power, the inverter 142 can be omitted and the AC power can be applied directly to the primary coil 144. The electronic device 104 and/or the base station 102 can include transformers for increasing or decreasing voltage, or various other circuit elements for power conditioning, voltage division, voltage regulation, etc.

FIG. 6 illustrates an exemplary power transfer scheme in which the power transmitter 140 of the base station 102 uses capacitive coupling to provide power to the power receiver 130 of the electronic device 104.

As shown, the base station 102 generally includes one or more electrodes 150 that can be positioned in proximity to and in alignment with one or more corresponding electrodes 152 of the electronic device 104. A DC input provided by the power source 136 can be converted by an inverter 142 into an AC signal which is in turn applied to the electrodes 150 of the base station 102. When the AC signal is applied to each electrode 150, an electric field forms between the electrode and its counterpart electrode 152 in the electronic device 104, effectively forming a capacitor. An AC signal is formed at the electrode 152 of the electronic device 104 by electrostatic induction, which is then converted by a rectifier 148 to a DC output that can be used to power the processor 122, memory 124, communications interface 128, or other components of the electronic device 104, or to charge a battery 126 of the electronic device. When the base station 102 is coupled to an AC mains current or other source of AC power, the inverter 142 can be omitted and the AC power can be applied directly to the electrodes 150. The electronic device 104 and/or the base station 102 can include transformers for increasing or decreasing voltage, or various other circuit elements for power conditioning, voltage division, voltage regulation, etc.

FIG. 7 illustrates an exemplary power transfer scheme in which the power transmitter 140 of the base station 102 uses ultrasound to provide power to the power receiver 130 of the electronic device 104.

As shown, the base station 102 generally includes a transducer configured to emit mechanical waves in response to an electric potential applied thereto by the power source 136. The transducer includes a piezoelectric element or crystal 154. The piezoelectric element 154 can be a single element or a phased array of elements. The piezoelectric element 154 can be coupled to an exterior wall of the base station chassis by a matching layer 156. The matching layer 156 can be configured to improve ultrasound transmission by reducing or eliminating the impedance mismatch between the piezoelectric element 154 and the sterile packaging 106, the air gap between the base station 102 and the electronic device 104, and the exterior walls of the base station and electronic device. The piezoelectric element 154 can also be mounted to a backing layer 158 to support and dampen the piezoelectric element.

The electronic device 104 can include a transducer configured to produce an electric potential when excited by ultrasound waves generated by the transducer of the base station 102. The transducer of the electronic device 104 can include any of the features of the transducer of the base station 102, including a matching layer 160, a piezoelectric element 162, and a backing layer 164. The output voltage generated at the transducer of the electronic device 104 can be rectified by a rectifier 148 and used to power the processor 122, memory 124, communications interface 128, or other components of the electronic device, or to charge a battery 126 of the electronic device. The electronic device 104 and/or the base station 102 can include transformers for increasing or decreasing voltage, or various other circuit elements for power conditioning, voltage division, voltage regulation, etc.

Ultrasonic power transfer can advantageously allow the electronic device to be wirelessly powered at greater distances and can be more tolerant of misalignment between the transmitter and receiver. Ultrasound can also be used to transfer power to a plurality of electronic devices simultaneously using a single base station.

In some embodiments, wireless power can be transferred to the power receiver 130 of the electronic device 104 from a source other than the base station 102.

In some embodiments, the power receiver 130 can include a solar or light-based charging unit, such as a photovoltaic cell, configured to convert photonic energy from the sun or other sources into electrical current for powering the electronic device 104. At least a portion of the sterile container 106 can be transparent, translucent, or otherwise configured to allow passage of light through the sterile container to the power receiver 130 of the electronic device 104. For example, the sterile container 106 can include a transparent or translucent window aligned with the power receiver 130 of an electronic device 104 contained within the sterile container. The base station 102 can include a light source configured to deliver photonic energy through the sterile container 106 to the power receiver 130 of the electronic device 104.

Figure 8:
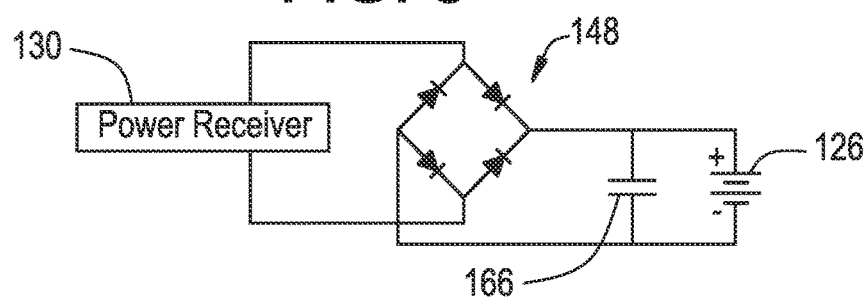
FIG. 8 is a schematic circuit diagram of a battery charging circuit.

FIG. 8 illustrates an exemplary embodiment of a battery charging circuit that can be included in the electronic device 104. As shown, the AC output of the power receiver 130 (e.g. a coil, an electrode, and/or a transducer) can be applied to a full-wave rectifier 148 to convert the AC output to a constant polarity signal which is then applied to one or more capacitors 166 configured to store electrical energy and slowly dissipate power into the battery 126 of the electronic device 104 to charge the battery. The illustrated circuit can advantageously yield a higher average output voltage and provide more consistent and efficient battery charging. The illustrated circuit can be used with any of the power transfer schemes discussed above.

Figure 9:
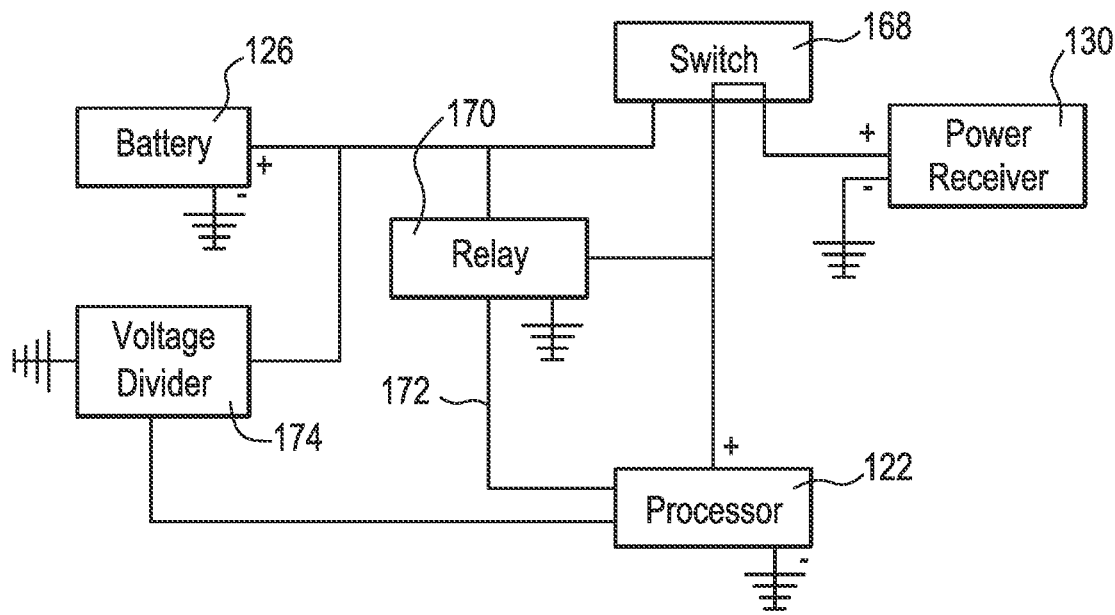
FIG. 9 is a schematic circuit diagram of a switching circuit in a first configuration.
Figure 10:
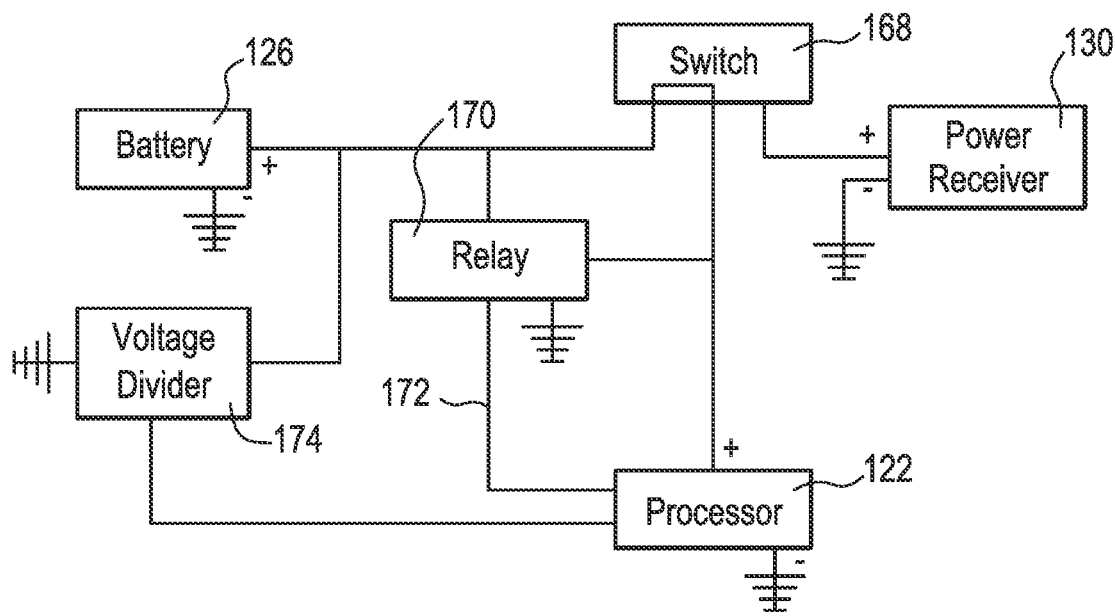
FIG. 10 is a schematic circuit diagram of the switching circuit of FIG. 9 in a second configuration.

FIGS. 9-10 illustrate an exemplary embodiment of a switching circuit that can be included in the electronic device 104. The switching circuit can include a switch 168 configured to change the circuit between first and second operating modes.

As shown in FIG. 9, the switch 168 can be disposed in a first position to place the circuit in a first operating mode. In the first operating mode, power from the power receiver 130 is supplied through the switch 168 to the processor 122 of the electronic device 104 to allow for operation or programming of the electronic device. Power from the power receiver 130 is also supplied through the switch 168 to a relay, transistor, or other switch 170 that can be selectively actuated by the processor 122 via a control line 172. The processor 122 can actuate the relay 170 to allow power from the power receiver 130 to pass through the relay to the battery 126 such that the battery can be charged. The processor 122 can also actuate the relay 170 to disconnect the battery 126 from the power receiver (e.g., when the battery is fully charged). The electronic device 104 can include a sense circuit for detecting the charge level of the battery 126, and the processor 122 can be configured to automatically switch the relay 170 to allow the battery to be charged from the power receiver 130 when the sense circuit determines that the battery charge is below a predetermined threshold level. For example, the electronic device 104 can include a voltage divider 174 that allows the processor 122 to take readings of the battery voltage and thereby detect the charge level of the battery 126.

As shown in FIG. 10, the switch 168 can be disposed in a second position to place the circuit in a second operating mode. In the second operating mode, the power receiver 130 is disconnected from the processor 122, the battery 126, and the other components of the electronic device 104. In addition, power from the battery 126 is supplied through the switch 168 to the processor 122 to allow for operation or programming of the electronic device 104. The processor 122 can continue to monitor the battery charge, e.g., via the voltage divider 174, and trigger a notification to the user when the battery charge drops below a predetermined threshold.

The switch 168 can be a manual switch actuated by a user (e.g., when the electronic device 104 is first removed from its sterile packaging 106 or when the electronic device is ready to be used). The switch 168 can also be an automatic switch configured to automatically toggle upon occurrence of a triggering event (e.g., removal of the electronic device 104 from its sterile packaging 106). Exemplary switches include toggle switches, pushbutton switches, pressure switches, proximity switches, temperature switches, and so forth. The electronic device 104 can be shipped from the manufacturer or other source with the switch 168 toggled to the first operating mode, such that the electronic device can be wirelessly powered and/or charged without removing the electronic device from its sterile package 106 or otherwise toggling the switch. Once the electronic device 104 is removed from its sterile package 106 and ready to be used in a procedure, or at any other desired time, the switch 168 can be toggled to the second operating mode to allow the device to be powered by its internal battery 126.

The systems described herein can be used in various ways to facilitate a medical, surgical, or other procedure.

In some embodiments, a sterile packed electronic device can be positioned on or near the base station and power can be transferred wirelessly from the base station to the electronic device. When wireless power is applied to the electronic device, the power can be used to charge an on-board battery of the electronic device. Accordingly, the battery of the electronic device can be fully charged in anticipation of a procedure, without opening the sterile packaging of the electronic device.

In some embodiments, a sterile packed electronic device can be positioned on or near the base station and power can be transferred wirelessly from the base station to the electronic device. When wireless power is applied to the electronic device, the processor of the electronic device can automatically wake and selectively couple a battery of the electronic device to the power receiver to charge the battery (e.g., based on a detected charge level of the battery).

In some embodiments, a sterile packed electronic device can be positioned on or near the base station and power can be transferred wirelessly from the base station to the electronic device. When wireless power is applied to the electronic device, the processor of the electronic device can automatically wake and activate the communications interface of the electronic device. The electronic device can then communicate with the base station or some other external device.

The communication can include transferring patient data to the electronic device to pre-program the device for a procedure.

The communication can include transferring procedure-specific data (e.g., a pre-operative plan or surgical correction information) to the electronic device to pre-program the device for a procedure.

The communication can include transferring operating software or firmware to the electronic device (e.g., for field upgrades of the electronic device's programming).

The communication can include executing a diagnostic routine by the processor of the electronic device and transferring the result of the diagnostic routine to the base station or another external device.

The communication can include transferring identification information of the electronic device to the base station or another external device.

The base station can be used to communicate with an electronic device after the electronic device is removed from a sterile container. For example, the base station can communicate with the electronic device after a medical procedure is performed. The base station can download measurements taken during the procedure, system diagnostic reports, and/or other information from the electronic device. Power for the communication can be provided wirelessly, which can allow the communication to occur with or without a battery of the electronic device being installed.

Before any of the above methods are performed, or at any other desired time, the electronic device can be sterilized and/or sealed in a sterile container. After any of the above methods are performed, or at any other desired time, the electronic device can be used in medical procedure, a surgical procedure, or some other procedure.

The systems and methods disclosed herein can, in at least some embodiments, provide for a number of advantages. For example, by providing a way to wireless charge an electronic device, the device's battery can be made smaller and the size and/or weight of the electronic device can be reduced. As another example, surgeons can use preoperative planning software and then download information into a sterile packed electronic device that is then brought to the operating room, opened using standard precautions, and delivered into the sterile field fully charged and containing data to perform the desired procedure.

Systems and methods disclosed herein can provide the ability for transfer of data (patient, product, or otherwise) to an electronic device while the device is still sterile packed without violating the sterile package or draining the packaged battery. This can reduce the need for operating room programming of devices which can improve both speed and flow in the operating room. This can also allow for patient specific data to be entered into "universal" electronic devices without compromising the package integrity.

Systems and methods disclosed herein can ensure that the charge/power of pre-packaged sterile electronic devices are ready for use. Battery transfer and battery life can be a frequent challenge for any electronic device utilized within the sterile field. Having a means to ensure that the device is fully charged prior to use in the operating room can prevent frustration and improve speed and ease of use.

In some instances, it can be desirable that the electronic device be powered outside the sterile field for identification and calibration. Systems and methods disclosed herein can maintain sterility while still allowing device setup well in advance of a procedure. Having a means to ensure that the device is set up and calibrated prior to use in the operating room can reduce wound exposure time, reduce number of steps, reduce setup errors, reduce frustrations, and improves speed and ease of use.

Systems and methods disclosed herein can allow power charging of sterile devices on the back-table of the operating room after being turned on for connection and calibration. Such systems can, in some embodiments, be switched through a relay or other device to battery power only when the device is brought into the sterile field. This can improve device use time, battery life, and power-management for long or unusual surgical cases.

Systems and methods disclosed herein can be used for incoming inspection of sterile finished packages from OEMs before the packages are accepted as inventory. In other words, systems and methods can allow for quick testing of devices inside the sterile pack for any malfunctions before the devices are distributed to users, which can improve out-of-the-box failure rate.

While use in medical and surgical procedures is generally contemplated herein, it will be appreciated that the systems and methods herein can be used for any of a variety of non-medical and/or non-surgical procedures.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present invention.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

The invention claimed is:

1. A system, comprising:
an electronic device having a wireless power receiver with an integrated communications interface, a sensor configured to detect a position or orientation of the electronic device, and an internal battery;
a sterile container in which the electronic device is disposed such that the sterile device is completely surrounded by the sterile container; and
a base station having a wireless power transmitter with an integrated communications interface, the wireless power transmitter being configured to transfer power through the sterile container to the wireless power receiver of the electronic device,
wherein the wireless power receiver of the electronic device is configured to receive and send information embedded or encoded in a wireless power signal between the electronic device and the base station, and
wherein the wireless power transmitter of the base station is configured to receive and send information embedded or encoded in the wireless power signal between the electronic device and the base station.

2. The system of claim 1, wherein the electronic device comprises at least one of an instrument and an implant.

3. The system of claim 1, wherein the sterile container includes a graphical mark positioned with respect to the power receiver such that, when the graphical mark of the sterile container is aligned with a graphical mark of the base station, the power receiver is aligned with the power transmitter.

4. The system of claim 1, wherein the base station includes a recess positioned with respect to the power transmitter such that, when the sterile container is seated in the recess, the power transmitter is aligned with the power receiver.

5. The system of claim 1, wherein the sterile container is configured to maintain the power receiver in a fixed position with respect to the sterile container.

6. The system of claim 1, wherein the sterile container comprises an inner blister pack in which the electronic device is disposed, an outer blister pack in which the inner blister pack is disposed, and an outer box in which the outer blister pack is disposed.

7. The system of claim 1, wherein the electronic device includes a switch configured to switch between a first operating mode in which the electronic device is powered by the power receiver and a second operating mode in which the electronic device is powered by an internal battery.

8. The system of claim 7, wherein the switch is configured to switch from the first operating mode to the second operating mode automatically when the electronic device is removed from the sterile container.

9. The system of claim 1, wherein the integrated communications interface of the base station is configured to wirelessly transmit medical data to the integrated communications interface of the electronic device via the wireless power signal, the medical data comprising at least one of patient-specific data, an operative plan, surgical correction information, and device calibration information.

10. The system of claim 1, wherein the integrated communications interface of the electronic device is configured to wirelessly transmit device data to a the integrated communications interface of the base station via the wireless power signal, the device data comprising at least one of device identification information, device diagnostic information, and device charge level information.

11. The system of claim 1, wherein the power transmitter comprises an ultrasonic transducer configured to generate ultrasonic waves received at an ultrasonic transducer of the power receiver to wirelessly transfer power from the base station to the electronic device.

12. The system of claim 1, wherein the power transmitter comprises a primary coil configured to generate a magnetic field between the primary coil and a secondary coil of the power receiver to wirelessly transfer power from the base station to the electronic device.

13. The system of claim 1, wherein the power transmitter comprises an electrode configured to generate an electric field between the electrode and an electrode of the power receiver to wirelessly transfer power from the base station to the electronic device.

14. The system of claim 1, wherein the power receiver comprises a full wave rectifier that rectifies an AC signal received at the power receiver and applies the signal to a capacitor of the electronic device wired in parallel with a battery of the electronic device to charge the battery.

15. The system of claim 1, wherein the integrated communications interfaces of the base station and the electronic device are configured to encode the information in the wireless power signal using at least one of: frequency modulation, frequency-domain multiplexing, frequency shift keying, amplitude modulation, phase modulation, analog or digital modulation techniques.

16. The system of claim 1, wherein the integrated communications interfaces of the base station and the electronic device comprise filters or other circuit elements configured to extract the information from the power signal or configured to embed information in the power signal.

* * * * *